(12) United States Patent
Bezvershenko et al.

(10) Patent No.: US 7,428,319 B2
(45) Date of Patent: Sep. 23, 2008

(54) IDENTIFICATION OF A PERSON BASED ON ULTRA-SOUND SCAN ANALYSES OF HAND BONE GEOMETRY

(75) Inventors: Zinayida Bezvershenko, 407-2361 Lakeshore blvd West, Toronto, Ontario (CA) M8V 1B7; Volodymyr Tchouikevitch, 412-2361 Lakeshore blvd West, Toronto, Ontario (CA) M8V 1B7; John Ghorayeb, 524 Village Parkway, Markham, Ontario (CA) L3R 9N5

(73) Assignees: Alojz (Al) Muzar - Click Into Inc., Richmond Hill, Ontario (CA); John Ghorayeb, Unionville, Ontario (CA); Volodymyr Tchouikevitch, Toronto, Ontario (CA); Zinayida Bezvershenko, Toronto, Ontario (CA)

( * ) Notice: Subject to any disclaimer, the term of this patent is extended or adjusted under 35 U.S.C. 154(b) by 679 days.

(21) Appl. No.: 10/910,303

(22) Filed: Aug. 4, 2004

(65) Prior Publication Data
US 2005/0069177 A1 Mar. 31, 2005

(30) Foreign Application Priority Data
Aug. 6, 2003 (CA) .................... 2438220

(51) Int. Cl.
*G06K 9/00* (2006.01)
(52) U.S. Cl. ................ 382/115; 382/209; 382/218

(58) Field of Classification Search ......... 382/115–124, 382/128, 209, 218, 224, 254, 154; 340/5.1, 340/5.81, 5.82; 713/186
See application file for complete search history.

(56) References Cited

U.S. PATENT DOCUMENTS

| | | |
|---|---|---|
| 3,576,537 A | 4/1971 | Ernst |
| 3,576,538 A | 4/1971 | Miller |
| 3,581,282 A | 5/1971 | Altman |
| 3,648,240 A | 3/1972 | Jacoby et al. |
| 3,882,462 A | 5/1975 | McMahon |
| 3,968,476 A | 7/1976 | McMahon |
| 3,975,711 A | 8/1976 | McMahon |
| 4,032,889 A | 6/1977 | Nassimbene |
| 4,206,441 A | 6/1980 | Kondo |
| 4,394,773 A | 7/1983 | Ruell |
| 4,537,484 A | 8/1985 | Fowler et al. |
| 4,573,193 A | 2/1986 | Shuto et al. |

(Continued)

FOREIGN PATENT DOCUMENTS

CA 2308381 11/1998

OTHER PUBLICATIONS

Skokowski Can Biometric Defeat Terror?, Stanford University, pp. 1-12, Feb. 2002.*

(Continued)

*Primary Examiner*—Daniel G Mariam
(74) *Attorney, Agent, or Firm*—Ogilvy Renault LLP (57) ABSTRACT

The invention disclosed provides a method of biometric identification of a person based on ultra-sound scan analyses of hand bones. For the purposes of identification/verification, a three dimensional (3D) ultra-sound scan of an individual's hand bones is acquired to compare the scan with those stored in the record carrier that can be placed on the host or a remote computer.

24 Claims, 9 Drawing Sheets

U.S. PATENT DOCUMENTS

| | | | |
|---|---|---|---|
| 4,720,869 A | | 1/1988 | Wadia |
| 4,736,203 A | * | 4/1988 | Sidlauskas ................. 340/5.53 |
| 4,792,226 A | | 12/1988 | Fishbine et al. |
| 4,857,916 A | | 8/1989 | Bellin |
| 4,977,601 A | | 12/1990 | Bicz |
| 5,045,940 A | | 9/1991 | Peters et al. |
| 5,073,950 A | | 12/1991 | Colbert et al. |
| 5,131,038 A | * | 7/1992 | Puhl et al. ................. 340/5.61 |
| 5,325,442 A | | 6/1994 | Knapp |
| 5,335,288 A | | 8/1994 | Faulkner |
| 5,483,601 A | | 1/1996 | Bicz |
| 5,515,298 A | | 5/1996 | Bicz |
| 5,647,364 A | | 7/1997 | Schneider et al. |
| 5,719,950 A | | 2/1998 | Osten et al. |
| 5,737,439 A | * | 4/1998 | Lapsley et al. .............. 382/115 |
| 5,787,187 A | * | 7/1998 | Bouchard et al. ........... 382/115 |
| 5,793,881 A | | 8/1998 | Stiver et al. |
| 5,892,838 A | | 4/1999 | Brady |
| 5,935,071 A | | 8/1999 | Schneider et al. |
| 6,092,192 A | | 7/2000 | Kanevsky et al. |
| 6,219,439 B1 | | 4/2001 | Burger |
| 6,219,639 B1 | | 4/2001 | Bakis et al. |
| 6,296,610 B1 | | 10/2001 | Schneider et al. |
| 6,336,045 B1 | | 1/2002 | Brooks |
| 6,343,140 B1 | | 1/2002 | Brooks |
| 6,421,453 B1 | * | 7/2002 | Kanevsky et al. ........... 382/115 |
| 6,483,929 B1 | | 11/2002 | Murakami et al. |
| 6,507,662 B1 | | 1/2003 | Brooks |
| 6,628,810 B1 | * | 9/2003 | Harkin ....................... 382/116 |
| 6,720,712 B2 | | 4/2004 | Scott et al. |
| 6,724,689 B2 | | 4/2004 | Koenig |
| 6,844,660 B2 | | 1/2005 | Scott |
| 6,862,253 B2 | | 3/2005 | Blosser et al. |
| 6,898,299 B1 | * | 5/2005 | Brooks ....................... 382/115 |
| 7,190,817 B1 | | 3/2007 | Schneider et al. |
| 7,236,616 B1 | | 6/2007 | Scott |
| 7,254,255 B2 | | 8/2007 | Dennis |
| 2002/0053857 A1 | | 5/2002 | Scott et al. |
| 2002/0162031 A1 | | 10/2002 | Levin et al. |
| 2003/0001459 A1 | | 1/2003 | Scott |
| 2003/0133596 A1 | | 7/2003 | Brooks |
| 2004/0088553 A1 | * | 5/2004 | Levin et al. ................. 713/186 |

OTHER PUBLICATIONS

Vitria "Sistemed Biometrics", pp. 1-23, 1999.*
S. Bianchi, C. Martinoli, D. Sureda and G. Rizzatto, "Ultrasound of the Hand," "European Journal of Ultrasound," 2001, vol. 14, No. 1, pp. 29-34.
R. D. Danese, A.A. Licata, "Ultrasound of the Skeleton: Review of its Clinical Applications and Pitfalls," "Current Rheumatology Reports," 2001, vol. 3, pp. 245-248.
T. Kahana, J. Hiss, P. Smith, "Quantitative Assessment of Trabecular Bone Pattern Identification," "Journal of Forensic Sciences," 1998, vol. 43, No. 5, pp. 1144-1147.
T. Kahana, J. Hiss, "Positive Identification by Means of Trabecular Bone Pattern Identification," "Journal of Forensic Sciences," 1994, vol. 39, No. 5, pp. 1325-1330.
Department of Computer Science, Hong Kong University of Science and Technology, Hongkong, 2003, 8 p.
S. A. Teefey, W.D. Middleton, M. I. Boyer, "Sonography of the Hand and Wrist," "Seminars Ultrasound, CT, and MRI," 2000, 21(3). pp. 192-204.

* cited by examiner

Bone Data Structure

List of Bone Cross-sections

Coordinate $Y_1$ $P_{11}(X_{11}, Z_{11})$, $P_{12}(X_{12}, Z_{12})$, . . ., $P_1m_1(X_1 m_1, Z_1m_1)$ Coordinate $Y_2$ $P_{21}(X_{21}, Z_{21})$, $P_{22}(X_{22}, Z_{22})$, . . ., $P_2m_1(X_2 m_2, Z_2m_2)$

• • •

Coordinate $Yn$ $P_{n1}(X_{n1}, Z_{n1})$, $P_{n2}(X_{n2}, Z_{n2})$, . . ., $P_nm_n(Xn m_n, Znm_n)$ Local Coordinate System Bone Integral Parameters

IDENTIFICATION OF A PERSON BASED ON ULTRA-SOUND SCAN ANALYSES OF HAND BONE GEOMETRY

BACKGROUND OF THE INVENTION

Biometric identification methods are ubiquitous and have been employed in many areas as a means of ensuring security through personal verification. Established biometric identification methods include the use of fingerprints, hand geometry, iris, retina, voice recognition, handwriting etc. Kumar et al (2003) identify limitations to the reliable use of some of these methods due to difficulty acquiring the necessary details to make correct verifications, or due to logistical problems in employing the method of verification in the same manner each and every time.

Wadia (U.S. Pat. No 4,720,869) and Sidlauskas (U.S. Pat. No 4,736,203) have explored the use of hand surface geometry for the purpose of biometric identification. Wadia's use of a two-dimensional optical scanner to process the data to develop invariable hand measurements, and Sidlauskas' use of a digitizing camera and a pair of orthogonal reflecting surfaces to obtain a three-dimensional image of a hand have both been successful methods for identification. However, since the application of these methods rely on the soft-tissue dimensions of the hand, these methods are limited by the potential environmental and physiological factors that may alter the dimensions of the surface of the hand. Moreover, trials with this methodology have revealed that it is possible to falsify authentication. Therefore, the proposed invention aims to eliminate such consequential details by focusing attention on the bone structure of the hand.

Traditionally, plain radiographs, CT, and MRI have been used to evaluate the hand and wrist. However, recent advances in technology have allowed ultrasound to be considered one of the first line imaging techniques in the assessment of this entity (Bianchi et al, 2001; Teefey et al, 2000). Ultrasound is an attractive option to analyze bone geometry because it is inexpensive, non-invasive, rapid and lacks the radiation exposure that often accompanies the traditionally preferred modalities (Danese & Licata, 2001).

The method of biometric identification of an individual based on ultra-sound scan analyses of hand bones is unique in its own characteristics, and attempts to overcome the limitations suggested by Kumar et al (2003). This new method uses a very inexpensive and safe means to acquire the data via ultra-sound scanning of the hand bones. Research has established that trabecular bone architecture is unique to each individual and stable enough to be used as a means for positive identification (Kahana et al, 1998; Kahana & Hiss, 1994). Therefore, this new method attempts to identify an individual based on his/her hand bone geometry, because hand bones are unique to each person, and because the method to acquire the data is inexpensive, safe, accurate, and a non-invasive tool.

BRIEF SUMMARY OF INVENTION

The proposed objectives for the disclosed invention are as follows:

To provide a new method for the identification of a person based on ultrasound scan analyses of hand bone geometry To provide a new method for three-dimensional modeling of human hand bone geometry.

To provide a new method for recognition of bone entities comprising a human hand bone geometry To provide a new method of normalization of hand bone data which increases reliability of identification A three dimensional (3D) ultra-sound scan of a person's hand's bones is acquired to compare the individual's data with those stored in the record carrier that can be placed on the host or a remote computer. After processing, the acquired data is reorganized into a structure that describes hand bone geometry in terms of separate bone entities. The data is further transformed to follow a template with a set of predefined parameters that will be referred to as the "normalized template". The normalized template is a canonical form that positions each bone entity into a predefined position in relation to its adjacent bone entities and moves the whole hand to a predefined position in relation to the absolute coordinate system. The main objective of the normalized template is to allow for a meaningful comparison of the acquired data to the stored data.

BRIEF DESCRIPTION OF DRAWINGS

FIG. 1—Identification Algorithm
FIG. 2—Normalized Template Building Algorithm
FIG. 3—Points As Derived From Bone Surfaces
FIG. 4—Hand Bones
FIG. 5—Bone Data Structure
FIG. 6—Thumb Data Structure
FIG. 7—Finger Data Structure
FIG. 8—Hand Data Structure
FIG. 9—Bone Base Plane and Local Coordinate System
FIG. 10—Hand Coordinate System
FIG. 11—3D Model of Hand Bone Normalized Template

DETAILED DESCRIPTION OF THE INVENTION

The following text provides a thorough description of the "Identification" and "Normalized Template Building" algorithms with reference to a number of figures for ease of explanation. For a brief overview of the aforementioned algorithms, please refer to FIG. 1 and FIG. 2 respectively.

Figure 1:
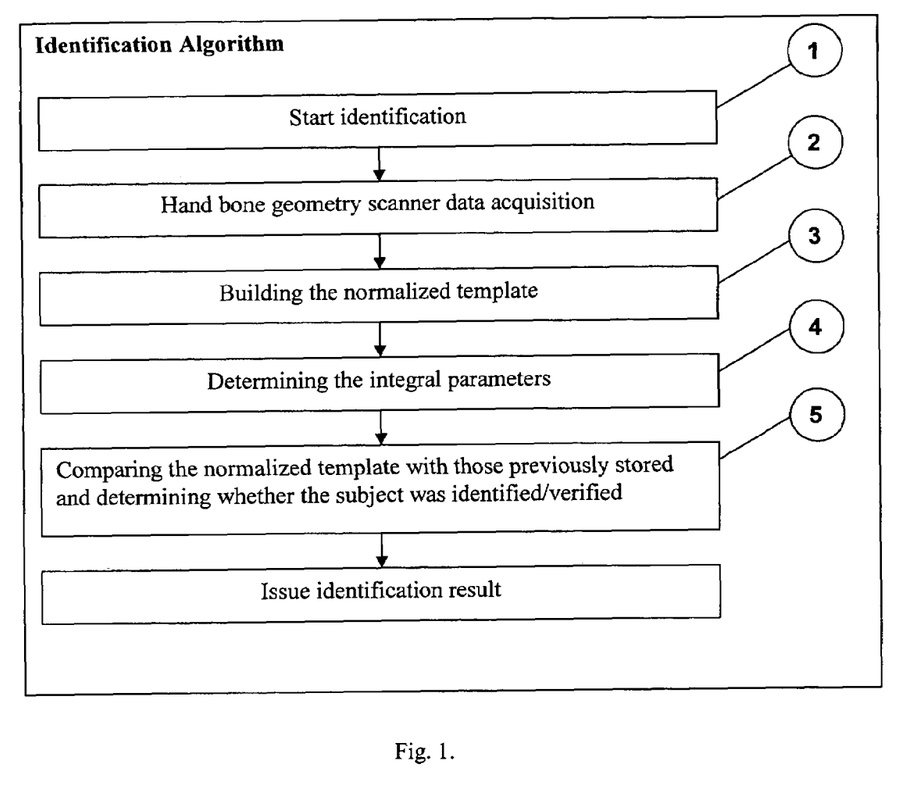

"Start Identification" [FIG. 1, Step 1]:

A person places either hand on the scanner platen for scanning. Once the subject chooses his/her left or right hand for scanning, at each subsequent identification attempt, the subject must use the same hand that was stored into the record carrier that can be placed on the host or a remote computer. In the case of a remote computer, the data can be searched through an existing network inclusive of wireless if available. The hand can be placed in any direction or location within the parameters of the scanner platen because the inventor-created normalization technique transforms scan data to the normalized template, which is then used in the process of comparing and judging whether the scan matches previously stored data in the record carrier. As mentioned above, the method is user-friendly and flexible in the sense that the person's hand does not need to be positioned in a fixed place and in a specific alignment to be scanned and processed for comparison. However, this method is not limited to other options such as fixed positioning by means of indicator, or an indentation or any other tool to achieve this task.

"Hand Bone Geometry Scanner Data Acquisition" [FIG. 1, Step 2]:

The hand bone geometry data is acquired using a freehand high-resolution ultrasound scanner. The present invention is not limited to any particular method or apparatus for transmitting ultrasonic energy. The process involves the acquisition of a set of 2D data that represents series of substantially parallel adjacent cross-section planes from throughout the volume of the hand with position data to locate the cross-section planes in space. Combination of these slices creates 3D data structures and images for volumetric data analysis. After "pre-processing" (a process that involves noise reduction and converting reflected ultrasound data from Polar coordinate system to Cartesian coordinate system), the acquired scan represents the coordinates of 3D points that are derived from the surfaces of the hand bones. The coordinates of points are defined in relation to the absolute coordinate system [see FIG. 3, #14] that is predefined by the scanner.

Figure 3:
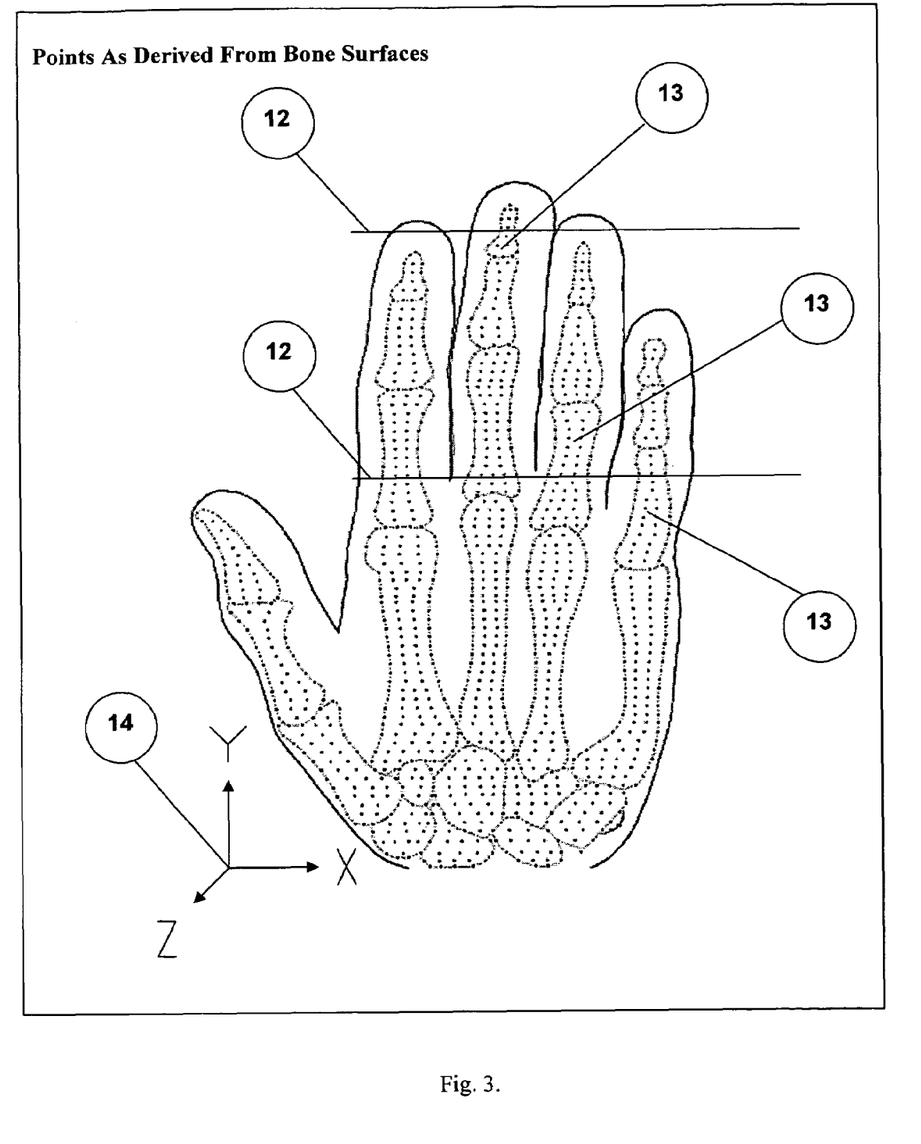

The suggested method, for descriptive purposes only considers that the cross-section planes are orthogonal to Y-axis that is directed [see FIG. 3] from the hand base to the tips of the fingers. The distance between planes is equal to a pre-set resolution tolerance. The sequence processing of data starts from the tips of the fingers but is not limited to other directions. Each cross-section [FIG. 3, #12] contains points [FIG. 3, #13] from the surfaces of all the bones that it runs through.

"Building the Normalized Template of the Hand Bone Set" [FIG. 1, Step 3]:

3.1. "Segregate Bone Entities from the Acquired Scanner Data" [FIG. 2, Step 6].

Figure 2:
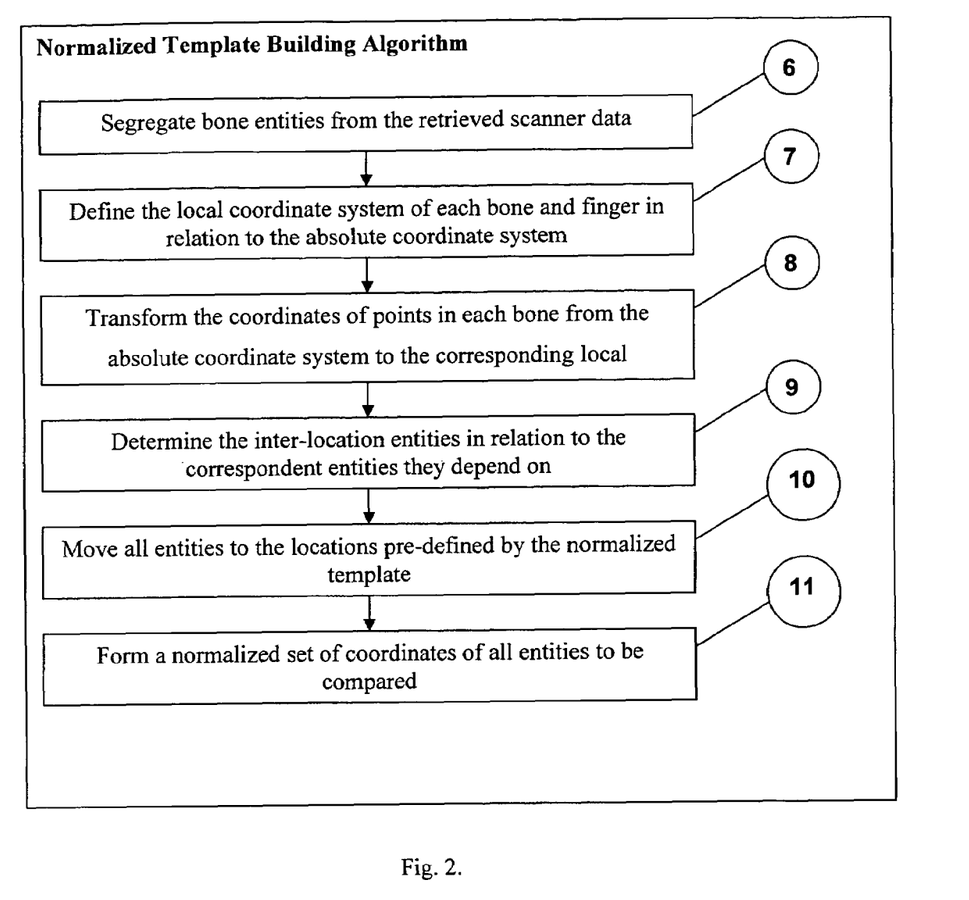

The Entity Segregation Algorithm assesses the values of the coordinates of points in relation to the location proximity and attributes the points to the appropriate bone entities.

Figure 4:
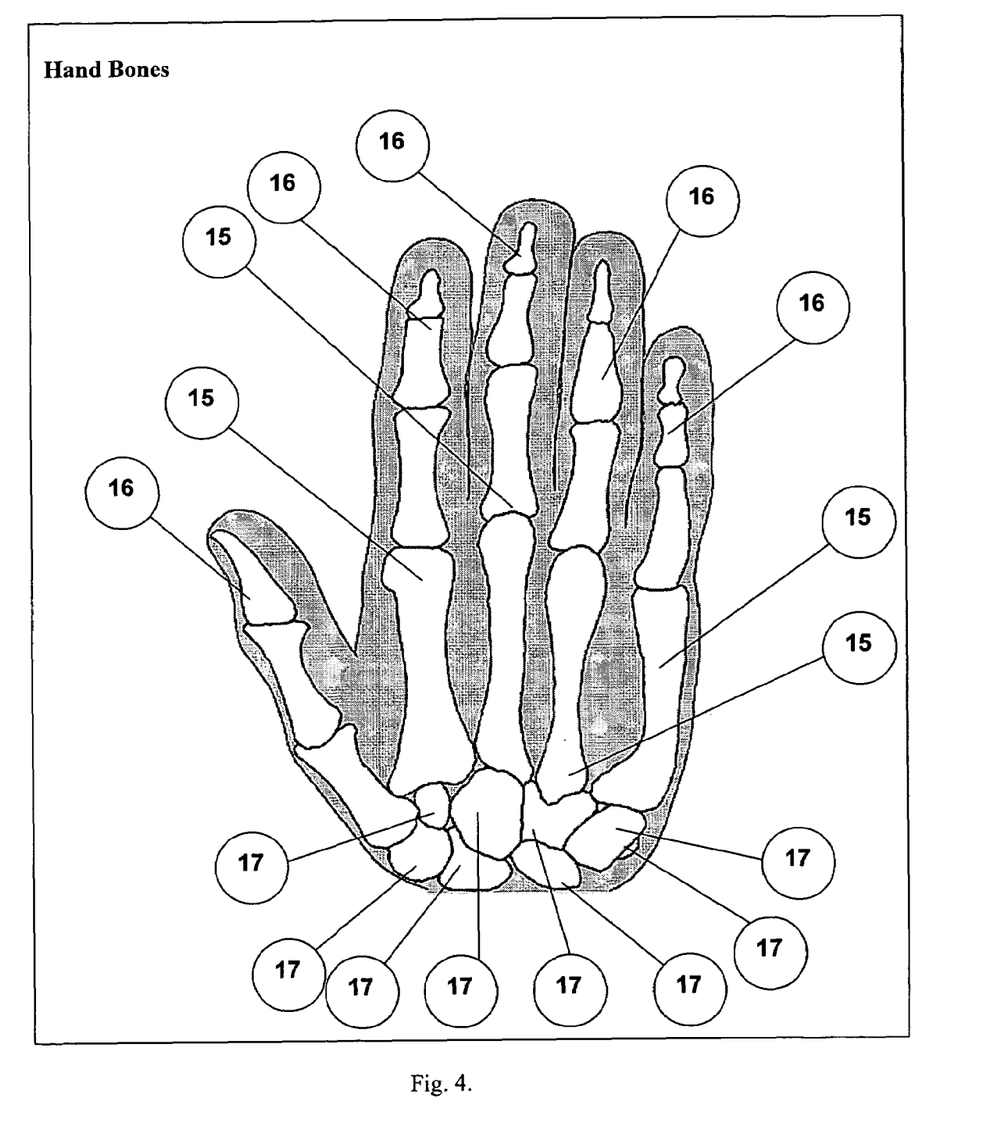

The purpose of this step of is to restructure the retrieved data into a set of entities that identifies all 27 bones of the hand (8 carpal bones [FIG. 4, #17], 5 metacarpal bones [FIG. 4, #15], and 14 phalanges [FIG. 4, #16]). The 5 metacarpal bones and 14 phalanges are then joined to form the entities known as the fingers.

The Sequence of Processing is as Follows:

Step one: Points are arranged by values of coordinate Y. Points with the same coordinate Y are then arranged by values of combinations of coordinates X & Z to form closed sequences defining the current cross-section of the bone surface.

Step two: Includes the operations of separating points of one bone entity from points of other bone entities along the X coordinate. The algorithm processes the values of coordinates within the pre-defined resolution tolerance and concludes the manner of grouping/segregating bone entities in relation to their location proximity. (i) If the location of two points is within the resolution tolerances, they are grouped in the same bone entity. (ii) If the distance along the X coordinate of the next point in line is greater than the resolution tolerance, it is grouped within the next bone entity. (iii) If the distance along the X coordinate is less than the tolerance, it is further analyzed by Z coordinates to assess the mode of direction. If the current direction is contrary to the previous direction with a steep gradient, then the point is grouped within the next bone entity, otherwise it is grouped in the same bone entity.

Figure 5:
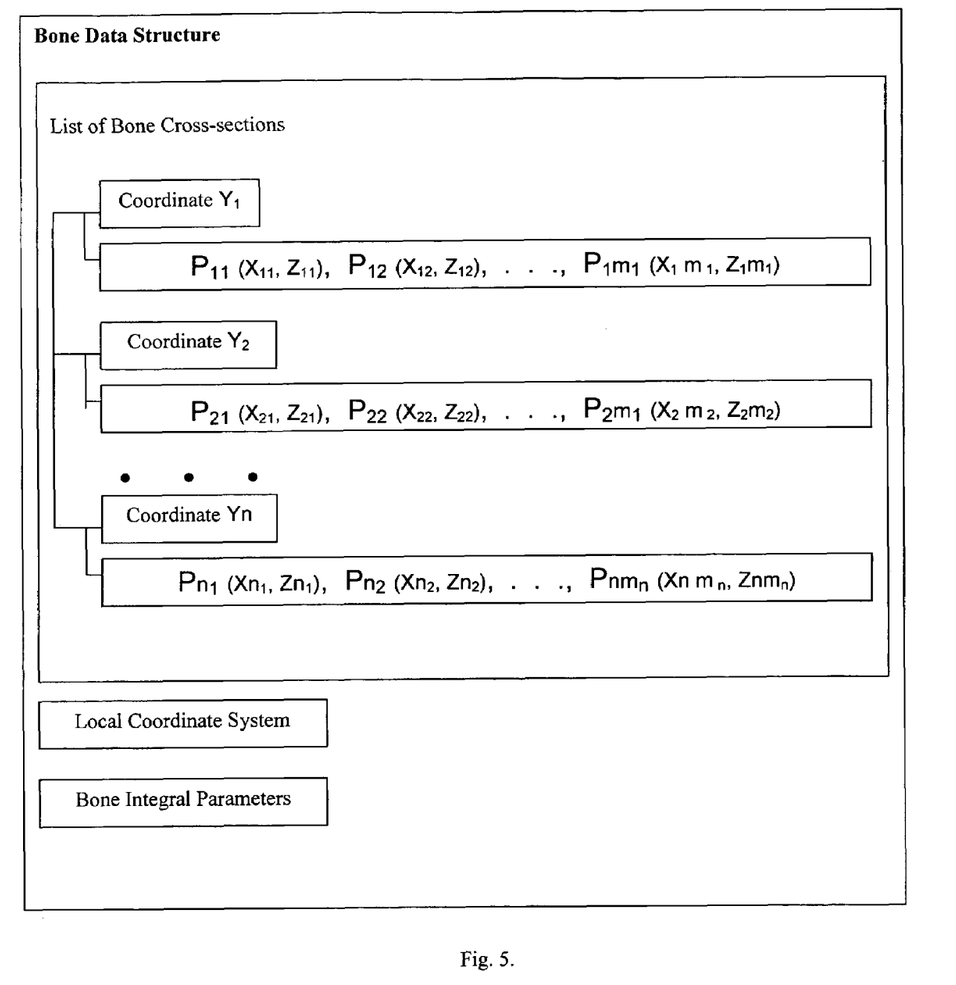

Step three: Deals with the categorization of a bone entity within a finger element, (i.e. separating the Distal, Middle, Proximal, and Metacarpal bones from each other). The algorithm analyzes the characteristics of points in terms of size, or area of cross-section of a particular sequence of points. A finger bone entity is defined by a set of cross-sections as illustrated in FIG. 5. The algorithm begins with the largest value of Y coordinates and ends with the smallest value of Y coordinates, and determines the diameter of each cross-section of the bone entity. The cross-section with the largest Y coordinate will define the start of the bone entity. Each diameter is then evaluated along the Y coordinate, and is added to the same entity, until the diameter value of the cross-section reaches the pre-defined 0 value. This Y coordinate will define the end of the current entity and the start of a new entity if it exists. This procedure is repeated to separate all the entities in a finger.

Segregation of the carpal bones is performed in a similar manner.

Bone data structure entails: Bone Cross-sections, Bone Integral Parameters, and the Local coordinate system, is illustrated in FIG. 5. Each element of the list of bone cross-sections consists of two members: a number that represent a value of Y coordinate of the cross-section that is common to its points, and a list of X, Z coordinates of all points of the cross-section. The number of points varies for different cross-sections, depending on their size. The set of integral parameters of a bone may contain but is not limited to measurements and calculated values to define the characteristics of a bone as a unit. The local coordinate systems of bone entities determine positions of the entities in relation to other bones that they depend on with an exception of carpal and metacarpal bones that depend only on the absolute coordinate system.

Figure 6:
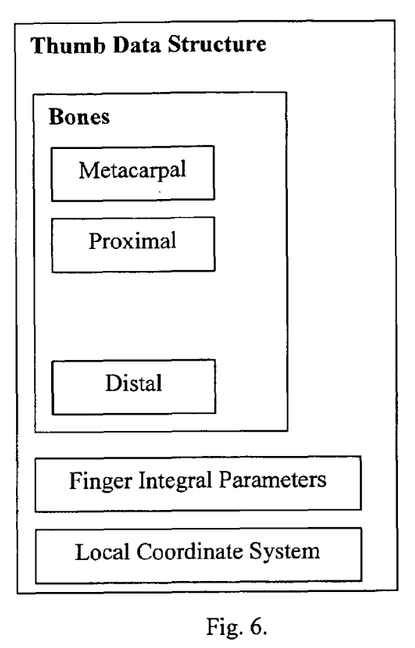
Figure 7:
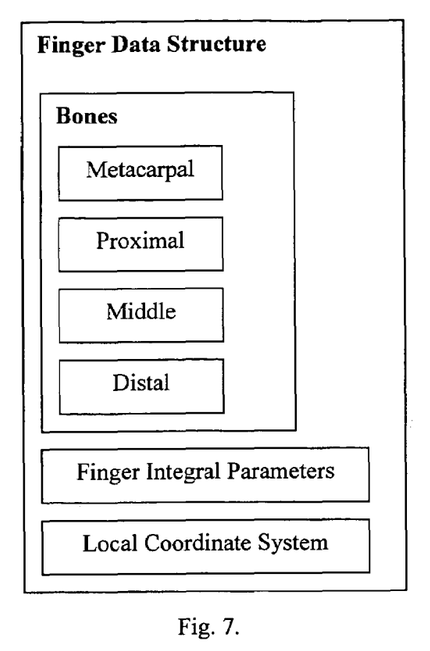

Thumb and Finger data structures as illustrated in FIG. 6 and FIG. 7 entails: Bones, Integral Parameters and the local coordinate system. The integral parameters and the local coordinate systems are represented in the same manner as those in the Bone Data Structure. The variance in structure is that the thumb has no middle phalange, whereas the finger consists of Distal, Middle, and Proximal phalanges, and Metacarpal bones. The local coordinate systems for the thumb and finger are coincident with those of the corresponding Metacarpal bones.

Figure 8:
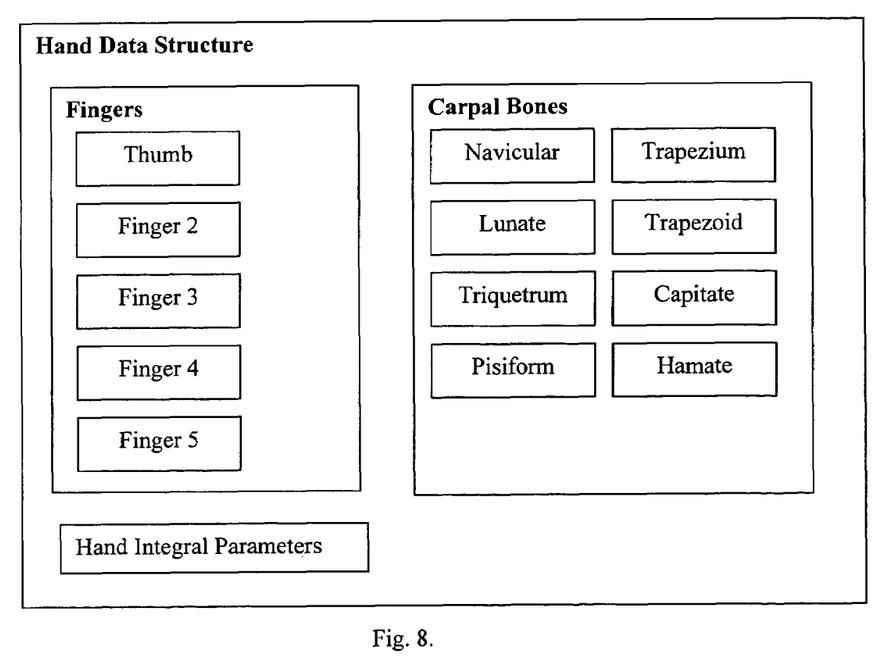

Hand Data Structure, and its components are illustrated in [FIG. 8]. Its integral parameters define the characteristics of the hand as an entity.

3.2. "Define the Local Coordinate System of Each Bone and Finger in Relation to the Absolute Coordinate System" [FIG. 2, Step 7]

Figure 9:
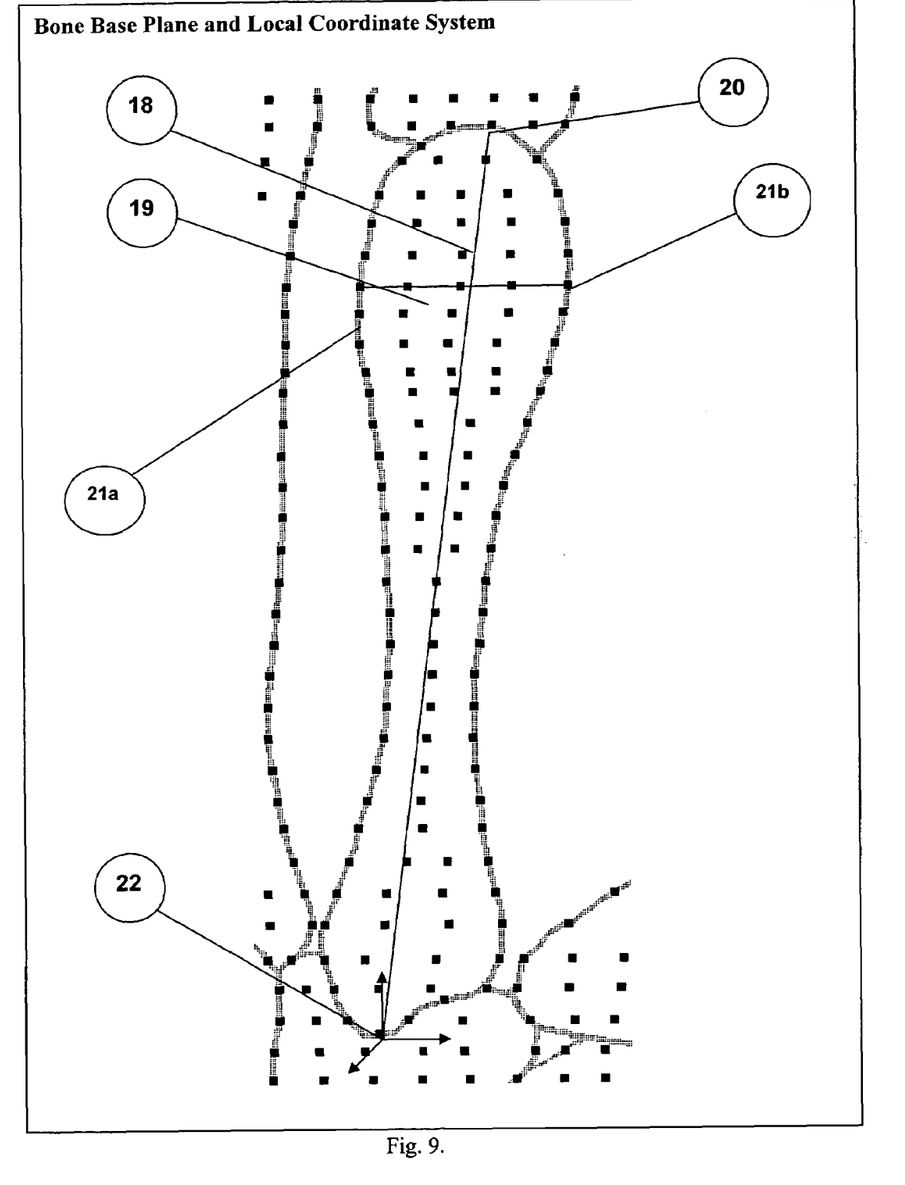

The algorithm seeks the two points at the surfaces of the bone entity with the largest distance between them, and sets an imaginary axis [FIG. 9, #18] between these two points. If there is more than one set of points that fits the profile of the imaginary axis #18, then the line joining the centers of two polygons formed by the ends of such lines would become the imaginary axis.

The algorithm then seeks the largest diameter of the bone [FIG. 9, #19] that is orthogonal to axis #18. It should be noted that if more than one diameter fitting the profile exists, then the method above applies.

Points #20, #21a and #21b of FIG. 9 will define the bone base plane. Point #21a and #21b represet the diameter #19. Point #20 represents the end of axis #18 that is closer to the tip of the hand. As the bone base plane is constant in relation to its bone entity, then it becomes the defining factors of positioning of the bone itself.

Point #22 the other end of axis #18 becomes the origin of the bone local coordinate system with its end preset with rotational angles in relation to the base plane.

Figure 10:
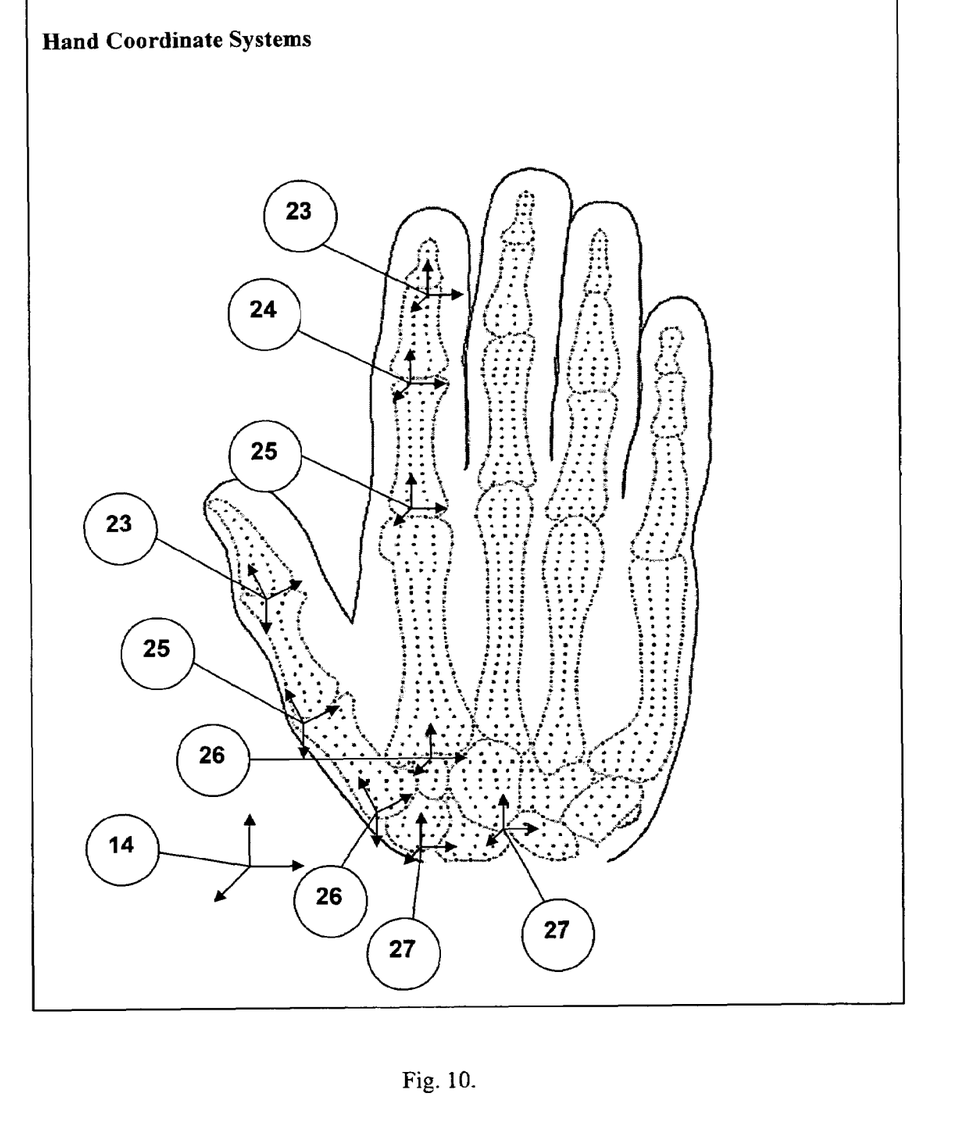

FIG. 10 illustrates the local coordinate systems of the bone entities.

The local coordinate systems of distal phalanges #23 determine positions of the entities in relation to the local coordinate system of the corresponding proximal phalange #25 of the thumb or of the middle phalange #24 of other fingers. Further, the local coordinate systems of the middle phalanges #24 determine positions of the entities in relation to the local coordinate system of the corresponding proximal phalanges

25 of the finger. The local coordinate systems of the proximal phalanges #25 determine positions of the entities in relation to the local coordinate system of the corresponding metacarpal bone #26 of the finger. And at last, the local coordinate system of each metacarpal bone and of the corresponding finger entities #26, and the local coordinate system of each carpal bone #27 determine positions of the entities in relation to the absolute coordinate system. The position of all coordinate systems are not limited to those that have been shown in FIG. 3, FIG. 9, and FIG. 10.

3.3. "Transform the Coordinates of Points in Each Bone from the Absolute Coordinate System to the Corresponding Local Coordinate System" [FIG. 2, Step 8]

The position of each local coordinate system relating to the absolute coordinate system is determined by its transformation matrix. To obtain the coordinates of points in relation to the local coordinate system, the vector defining these points in the absolute coordinate system is multiplied by the inverted transformation matrix.

3.4. "Determine the Inter-Location Entities in Relation to the Corresponding Entities they Depend on" [FIG. 2, Step 9]

The location is calculated for entities that belong to the same finger and depend on each other. These inter-locations are compared with the inter-location that has been chosen for a normalized template and the corresponding transformation matrices are formed.

3.5. "Move all Entities to the Locations Pre-Defined by the Normalized Template" [FIG. 2, Step 10]

Via the stepwise process of multiplying the vectors defining the location of bone entities to the corresponding transformation matrices, the algorithm moves all bone entities to the locations predefined by a definition of the normalized template.

This way the method accounts for possible rotations of distal phalange in relation to the corresponding proximal bone of the thumb or the corresponding middle phalange of other fingers comparing with the pre-defined normalized template inter-locations. The algorithm then accounts for possible rotations of all distal and middle phalanges of all fingers except the thumb in relation to the corresponding proximal phalanges, comparing with the pre-defined normalized template inter-locations. After that the algorithm accounts for possible rotations of all distal, middle, and proximal phalanges of all fingers (or distal and proximal phalanges for the thumb) in relation to the corresponding metacarpal bones comparing with the pre-defined normalized template inter-locations of these entities. This way the method accounts for possible combined rotations of fingers in relation to the corresponding metacarpal bones.

Further, for the set of carpal and metacarpal bones, their positions relating to the absolute coordinate system are compared with the positions that have been chosen in a normalized template. If the positions are different, the corresponding transformation matrix is formed and all these bones and all finger bones that depend on them are moved to the location pre-defined by the definition of the normalized template. This way, the method accounts for possible rotations and translation of whole hand in relation to the pre-defined location at the scanner platen.

As a result, all coordinates of all points of the bones have been accordingly changed to meet the conditions of the normalized template.

3.6. "Form a Normalized Set of Coordinates of all Entities to be Compared" [FIG. 2, Step 11]:

At this stage, all the bone entities are defined by the cross-sections that were perpendicular to the Y-axis as it was defined in the data set acquired from the scanner. However since acquisition, all bone entities may drift location. The algorithm is designed to redefine all points at the surfaces of bone entities accounting for such a drift to place them at the same pre-defined cross-section planes.

These new points are placed at the same locations for every scanning attempt allowing for the comparison of the content of data received from different sources.

Now the algorithm has finished building of the normalized template [see FIG. 1, step 3].

Figure 11:
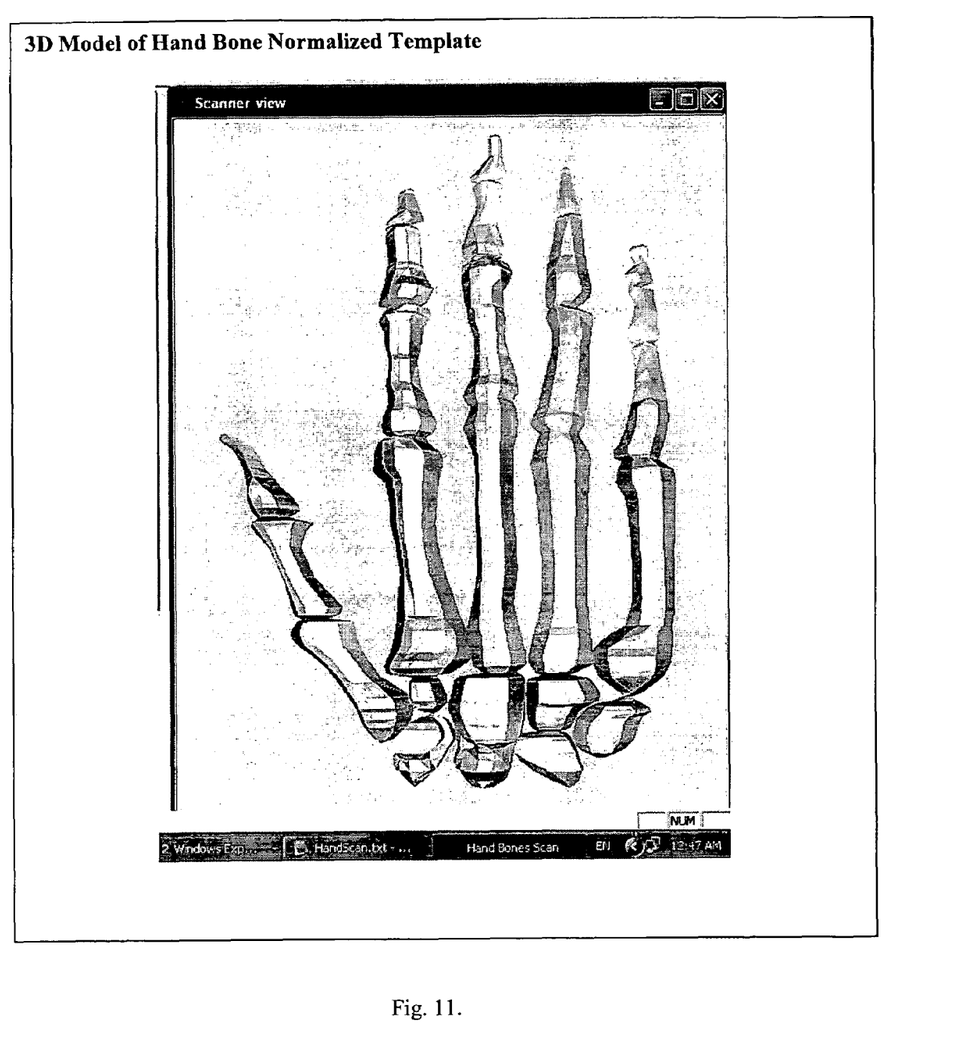

FIG. 11 illustrates a three dimensional projection of 3D model of a hand bone transformed along a normalized template as it is produced by an inventor-created Surface Rendering Algorithm. This algorithm is optionally used when the new hand bone template is recorded. To produce this image, the Surface Rendering Algorithm was created that forms a surface of the entities approximating it by triangular polygons. The algorithm creates the surface by rendering a sets of polygons to the screen accordingly to the sequence of the points of each couple of adjacent cross-sections.

"Determining the Integral Parameters" [FIG. 1, Step 4]:

The algorithm starts with a calculation of the bone integral parameters. These parameters may include, but are not limited to simple measurements such as length/width of a bone or a group of bones, or some results of calculations such as ratio of length to width or other more complex mathematical processing.

The algorithm proceeds with a calculation of the fingers integral parameters using the previously calculated bone integral parameters.

Next, it calculates the hand integral parameters using the previously calculated bone and finger integral parameters "Comparing the Normalized Template with those Previously Stored and Determining Whether the Subject was Verified/Identified" [FIG. 1, Step 5]:

The algorithm searches in the record carrier for a template that is identical to the obtained normalized template. This process can be accomplished in different ways. In the case of the identification task, the search may be accelerated using the key string built on the base of the integral parameters.

In case of verification, a person shall present by any means his/her identity information. The system will direct the search to the location of the record carrier, to identify the corresponding template of the person in preparation for comparing the verification attempt with the identity record. If no such identity record exists, or the identity of the person attempting the verification is falsified, then the verification will be rejected.

What is claimed is:

1. A method for identifying a person based on ultrasound scan analysis of bone geometry of the person, the method comprising the steps of:
    a) scanning a volumetric region of the person using ultrasound;
    b) acquiring three-dimensional geometric data of the bone geometry of the volumetric region;
    c) comparing the acquired three-dimensional geometric data previously stored geometric data to determine if a match exists.

2. The method as defined in claim 1 wherein the previously stored three-dimensional geometric data is retrieved by entering a personal identification number of the person.

3. The method as defined in claim 1, wherein the volumetric region comprises a plurality of bones, and before the comparing step c), the acquired data is restructured into separate bone entities corresponding to the bones in the volumetric region.

4. The method as defined in claim 3, wherein the acquired data comprises fewer bone entities than the previously stored data.

5. The method as defined in claim 3, wherein the volumetric region comprises a hand and the bone entities are categorized within different hand elements.

6. The method as defined in claim 3 further comprising the steps of:
   i) defining a local coordinate system for each bone entity in relation to an absolute coordinate system of the volumetric region;
   ii) transforming the acquired data for each bone entity from the absolute coordinate system to their respective local coordinate systems;
   iii) determining relative locations of the bone entities based on a normalized template; and iv) transforming the acquired data so as to move the bone entities to their relative locations.

7. The method as defined in claim 6, further comprising the step of redefining the acquired data to account for drift.

8. The method as defined in claim 6, further comprising the step of determining integral parameters of at least one of the bones to be used in the comparing step c).

9. The method as defined in claim 6, wherein the normalized template defines the geometry of a hand.

10. The method as defined in claim 1, wherein the volumetric region is placed on a scan platen prior to the scanning step a).

11. The method as defined in claim 10, wherein the volumetric region comprises a hand.

12. The method as defined in claim 1, wherein the acquired data comprises a combination of cross-sectional data within a plurality of planes extending through the volumetric region.

13. The method as defined in claim 12, wherein before the comparing step c), the acquired data is subjected to a noise reduction process and three-dimensional points representing the bone geometry are identified.

14. The method as defined in claim 1, further comprising the step of determining integral parameters of the bone geometry to be used in the comparing step c).

15. A method for identifying a person based on ultrasound scan analysis of bone geometry of a hand of the person, the method comprising the steps of:
   a) scanning the hand of the person using ultrasound;
   b) acquiring cross-sectional data within a plurality of planes extending through the hand;
   c) subjecting the cross-sectional data to a noise reduction process and identifying points representing the bone geometry of the hand;
   d) grouping the points into separate bone entities corresponding to bones in the hand;
   e) defining a local coordinate system for each bone entity in relation to an absolute coordinate system of the hand;
   f) transforming the points for each bone entity from the absolute coordinate system to their respective local coordinate systems;
   g) determining relative locations of the bone entities based on a normalized template;
   h) transforming the points so as to move the bone entities to their relative locations; and
   i) comparing the to previously stored geometric data to determine if a match exists.

16. The method as defined in claim 15, wherein the hand is positioned in a predefined location prior to the scanning step a).

17. The method as defined in claim 15, wherein the stored geometric data is retrieved using a personal identification number of the person.

18. The method as defined in claim 15, wherein the comparing step i) comprises comparing integral parameters of the bone geometry, determined based on the points, with the stored geometric data.

19. A method for verifying a person's identity based on ultrasound scan analysis of bone geometry of a hand of the person, the method comprising the steps of:
   a) retrieving previously stored geometric data the hand of the person;
   b) scanning the hand of the person using ultrasound;
   c) acquiring three-dimensional geometric data of the bone geometry of the hand;
   d) comparing the acquired three-dimensional geometric data to the previously stored geometric data to determine if a match exists.

20. The method as defined in claim 19, wherein before the comparing step d), the acquired data is restructured into separate bone entities and the bone entities are categorized within hand elements.

21. The method as defined in claim 20, further comprising the step of determining integral parameters of the bone geometry to be used in the comparing step c).

22. The method as defined in claim 20, wherein the previously stored three-dimensional geometric data is retrieved using a personal identification number of the person.

23. The method as defined in claim 22, wherein the stored geometric data is retrieved from a remote record carrier via wireless communication.

24. The method as defined in claim 19, wherein the volumetric region is placed on a scan platen prior to the scanning step b).

* * * * *